United States Patent [19]
Nijkerk et al.

[11] Patent Number: 5,177,076
[45] Date of Patent: Jan. 5, 1993

[54] AQUEOUS FOLINATE SOLUTION STABLE AT REFRIGERATOR TEMPERATURE, AS WELL AS PROCESS FOR ITS PREPARATION

[75] Inventors: Alfred J. Nijkerk, Amsterdam; Johanna M. P. Vermeer, Lisse, both of Netherlands

[73] Assignee: Pharmachemie BV, Haarlem, Netherlands

[21] Appl. No.: 440,129

[22] Filed: Nov. 21, 1989

[30] Foreign Application Priority Data

Jun. 6, 1989 [NL] Netherlands ............. 8901432

[51] Int. Cl.$^5$ ............................. A61K 31/495
[52] U.S. Cl. ............................. 514/249; 514/970
[58] Field of Search ............. 514/249, 920

[56] References Cited

U.S. PATENT DOCUMENTS

| | | | |
|---|---|---|---|
| 2,695,860 | 11/1954 | Weidenheimer et al. | 514/249 |
| 4,344,940 | 8/1982 | Chow et al. | 424/241 |
| 4,436,738 | 3/1984 | Bequette et al. | 424/238 |

FOREIGN PATENT DOCUMENTS 2381047  9/1978  France.

OTHER PUBLICATIONS

Bundesverband der Pharmazeutischen Industrie "Roto Liste", 1989, Editio Cantor, Aulendorf/Wurtt., De No. 12-022 Leucovorin.

Journal of Phamaceutical Sciences, vol. 69, No. 2, Feb. 1980, blz. 234, American Pharmaceutical Assocation; K. R. Scott et al.: "Drug interactions I: folic acid and calcium gluconate".

Primary Examiner—Frederick E. Waddell
Assistant Examiner—T. J. Criares
Attorney, Agent, or Firm—Ladas & Parry

[57] ABSTRACT

An aqueous folinate solution stable at refrigerator temperature is provided which contains folinate ions, complexed calcium ions, and if desired free calcium ions in a total amount of more than 12 mg/ml, as well as anions of a complexing agent for calcium. This solution is prepared by incorporating the complexing agent therein.

8 Claims, No Drawings

AQUEOUS FOLINATE SOLUTION STABLE AT REFRIGERATOR TEMPERATURE, AS WELL AS PROCESS FOR ITS PREPARATION

BACKGROUND OF THE INVENTION

The invention relates to an aqueous folinate solution which is stable at refrigerator temperature.

Folinic acid is a metabolite of folic acid and is the active form to which folic acid is converted in the body. This conversion is inhibited by some cytostatic agents, such as methotrexate. In order to counteract this it is necessary to administer folinic acid, and the form of the folinic acid which should be administered pharmaceutically is the calcium folinate.

Usually, calcium folinate is administered by infusion or injection, and the dosages thereof are growing ever higher. Consequently, there is a demand for more concentrated solutions. Calcium folinate is good soluble at room temperature, but it is not stable and consequently cannot be stored sufficiently long. At refrigerator temperature, at which it is much more stable, high concentrations cannot be prepared. At the normal refrigerator temperature of 4° C. crystallization may already occur at 15 mg/ml, and if by chance the refrigerator has been adjusted somewhat to the cold side and has a temperature of about 0° C., this may already occur at 12 mg/ml. Consequently, there is a need for an aqueous folinate solution which is stable at refrigerator temperature, i.e. which will not crystallize at that temperature.

SUMMARY OF THE INVENTION

It has now been found that much higher concentrations of folinate can be incorporated in the solution without a risk for crystallization in the refrigerator, if the calcium is complexed.

Therefore the invention provides an aqueous folinate solution stable at refrigerator temperature, which contains folinate ions and complexed calcium ions and possibly free calcium ions in a total amount of more than 12 mg/ml and furthermore anions of a complexing agent for calcium. In this way solutions can be prepared which can be stored in the refrigerator and contain even 50 mg/ml of folinate. If one wishes to store them at room temperature, at which of course the storage time is much shorter, one can even arrive at a maximum of 100 to 120 mg/ml.

DESCRIPTION OF PREFERRED EMBODIMENTS

Of course, the maximum effect of the complexing agent is attained, if this is added in a molar equivalent amount with respect to the calcium folinate. Per se there is no objection against using more of the complexing agent, provided for the rest this has no detrimental side-effects, but of course no advantages are obtained from such a greater amount.

In principle any complexing agent for calcium can be used which is admissible for therapeutical administration. The agent which is preferred and enters into consideration in the first place is ethylenediamine tetra acetic acid (EDTA) in the form of the di- or tetrasodium salt. The result of the use thereof is thus that the obtained solution contains ions, complexed calcium ions and possibly free calcium ions as the cations, and as the anions folinate ions and ethylenediamine tetraacetate ions. Briefly stated, the calcium is thus entirely or partially exchanged for sodium. This has no effect on the activity, because the folinic acid is the active substance.

The suitable pH range of the solution is the same as that of less concentrated solutions without complexing agent, i.e. generally 4.0-8.8, preferably 5.5-8.8 and especially 6-8. A complexing agent like EDTA has little or no influence on the stability of the obtained solution.

The following, non-limiting examples elucidate the invention by way of illustration only.

EXAMPLE I

A solution is prepared containing per ml the following ingredients:

| | |
|---|---|
| anhydrous calcium folinate (corresponding to 25 mg of folinic acid) | 27.01 mg |
| disodium EDTA-2H$_2$O | 19.67 mg |
| water for injection | 1.0 ml |

The obtained solution has a pH of 7.8.

EXAMPLE II

A solution is prepared which contains per ml the following:

| | |
|---|---|
| anhydrous calcium folinate (corresponding to 25 mg folinic acid) | 27.01 mg |
| disodium EDTA-2H$_2$O | 5.08 mg |
| water for injection | 1.0 ml |

The obtained solution has a pH of 7.8.

The solutions of both examples can be made isotonic by addition of NaCl.

As appears from example II, addition of sodium EDTA in an amount of about 25% of the molar equivalent amount already yields a solution which contains considerably more than 20 mg/ml of folinate. This solution does not crystallize in the refrigerator, as has been established experimentally. If desired, considerably greater amounts of folinate can be incorporated in the solution of example I than has been done in this example; the concerning experiment was carried out in the first place for orienting purposes.

We claim:

1. In an aqueous folinate solution containing folinate ions and calcium ions, wherein the solution is stabilized by refrigeration, the improvement comprising having the folinate ions and calcium ions present in a total amount of more than 15 mg/ml, said solution further comprising anions of a complexing agent for calcium, sufficient of said anions of said complexing agent being present and being complexed with the calcium ions to prevent crystallization of said solution at temperatures as low as about 0° C.

2. Solution according to claim 1, wherein the anions of the complexing agent are present in a molar equivalent amount with respect to the folinate ions.

3. Solution according to claim 1, wherein the anions of the complexing agent are ethylenediamine tetra-acetate ions.

4. Solution according to claim 2, wherein the anions of the complexing agent are ethylenediamine tetra-acetate ions.

5. In a process for refrigerating an aqueous calcium folinate solution comprising folinate ions and calcium ions to enhance the stability of the solution, the improvement comprising including in said solution folinate ions and calcium ions in a total amount of more than 15 mg/ml and adding to the solution a complexing agent for calcium in an amount sufficient to prevent crystallization of said solution at temperatures as low as about 0° C.

6. A process according to claim 5, wherein the complexing agent is used in a molar equivalent amount with respect to the calcium folinate.

7. A process according to claim 5, wherein a sodium salt of ethylene-diamine tetra-acetic acid is chosen as the complexing agent.

8. A process according to claim 6, wherein a sodium salt of ethylene-diamine tetra-acetic acid is chosen as the complexing agent.

* * * * *